US00PP08457P

United States Patent [19]

Kientzler

[11] Patent Number: Plant 8,457

[45] Date of Patent: Nov. 9, 1993

[54] IMPATIENS PLANT NAMED PAPETE

[75] Inventor: Ludwig Kientzler, Gensingen, Fed. Rep. of Germany

[73] Assignee: Paul Ecke Ranch, Inc., Encinitas, Calif.

[21] Appl. No.: 872,340

[22] Filed: Apr. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer
*Assistant Examiner*—E. F. McElwain
*Attorney, Agent, or Firm*—Foley & Lardner

[57] ABSTRACT

A new and distinct cultivar of Impatiens plant named Papete, characterized by its large, purplish-red flowers, compact growth habit with a tight branching habit requiring no pinching, green glossy foliage, very early and uniform flowering, floriferous habit, and by its suitability to pot or hanging basket culture.

1 Drawing Sheet

The present invention relates to a new and distinct cultivar of plant known as Impatiens and commercially known as New Guinea Impatiens. The new cultivar is known by the cultivar name Papete, and was developed by the inventor Ludwig Kientzler in Gensingen, Federal Republic of Germany by crossing the cultivar designated D-15 (seed parent) with the cultivar designated D-603 (pollen parent).

Asexual reproduction by terminal (stem tip) cuttings taken by me or under my supervision at Gensingen, Federal Republic of Germany, has shown that the unique features of this new Impatiens are stabilized and are reproduced true to type in successive propagations.

The following characteristics distinguish the new Impatiens from both its parent varieties and other cultivars of this general type known and used in the floriculture industry:

. Very compact with a tight branching habit. Plants in 16.5 cm pots were 15 cm tall and 28 cm wide, eight weeks after planting.
2. Large, purplish-red flowers. Open flowers measure up to 6 cm or more in diameter.
3. Early flowering and very floriferous. Plants in 16.5 cm pots were in flower 6 weeks after planting.
4. Green, glossy foliage.
5. Well suited both to 4" pot and 8" hanging basket culture.

The flower color of Papete is much redder than Bora Bora, disclosed in a pending application of applicant. The flower color of Papete is similar to Mimas, disclosed in U.S. Plant Pat. No. 6,925, but the growth habit of Papete is much more compact, and Papete flowers earlier with larger flowers than Mimas.

The accompanying colored photograph is a top perspective view of the new cultivar, showing color as true as it is reasonably possible to obtain in a colored reproduction of this type.

The following is a detailed description of my new Impatiens cultivar based on plants grown under commercial practice in Encinitas, Calif. Plants were started as rooted cuttings and were transplanted in mid-December into 16.5 cm (6.5 inch) pots, one pot per plant. By mid-February, plants were growing vigorously and were in flower. The values, measurements and observations noted below were taken from plants in full bloom in mid-February.

Color references are made to The Royal Horticultural Society Colour Chart (RHS), except where general terms of ordinary dictionary significance are used.

Parentage: Cross between D-15 (seed) and D-603 (pollen).

Asexual reproduction:

A. *Cutting type.*—Tip, with stems 2–3 cm long developing to 4–5 cm after 21 days in propagation.

B. *Time to initiate roots.*—8–10 days at 23° C.; nicely developed root mass in 18–21 days.

C. *Rooting habit.*—Numerous, fibrous, adventitious roots from the stem.

Plant description:

A. *Form.*—Symmetrical, bush shaped, flowering herb, with self-branching characteristics giving the plant a full appearance. Pinching is not recommended since it does not enhance branching and only delays flowering by removing flower buds.

B. *Habit of growth.*—Vigorous, self-branching habit, producing whorls of leaves and flowers. Growth is indeterminate and flowering is continuous.

C. *Foliage description.*—Leaves are simple. Lower leaves on stems are opposite. Higher leaves in whorls of 3–5, but predominantly 5. 1. Leaf shape: Ovate. Leaf blade tips are acuminate; bases are acute. 2. Leaf blade size: Mature leaves are approximately 10 cm long and 4 to 4.5 cm wide. 3. Petiole length: About 4 cm. 4. Leaf margin: Very finely ciliated and finely serrated. 5. Leaf texture: Slightly rugose. a. Upper surface: Glabrous. b. Under surface: Glabrous, but with small setae on leaf veins. 6. Leaf color: Glossy green with purple overtones. Petioles are reddish. a. Upper surface: Near 147A. b. Under surface: Greyed-green, between 191A and 191B. 7. Venation: Pinnate contrasting with leaf under surface.

Flowering description:

A. *Flowering habits.*—Very floriferous. Flowering is continuous. Flowers develop progressively around the whorl of leaves, taking 5–7 days from buds which show color, to bloom. Flowers are single and large, lasting for 2–3 weeks.

B. *Natural flowering season.*—Flowering is indeterminate and occurs throughout the year. Quantity of flowers increases with increasing light intensity and duration. However, floriferousness may wane during hot summer days in temperate climates.

C. *Flower buds.*—Ellipsoidal and covered with 3 sepals plus 2 rudimentary sepals fused into the under surface of the superior petal. A spur originates from the base of the inferior sepal. Spur is red and approximately 5.5 to 6 cm long.

D. Flowers borne.—Singly, on reddish pedicels 5–6 cm long.

E. *Quantity of flowers.*—Usually one flower per leaf. Flowers occur progressively around the whorl of leaves so that tight buds to mature flowers are visible at the same time.

F. *Petals.*—Petals open nearly perpendicular to the pedicel so the plane of the flower surface is nearly flat. 1. Number of petals: Five (5) petals, all overlapping. 2. Shape: All petals are heart-shaped. Superior petal has a broad base. Other petals have a pointed base. 3. Color: Purplish-red. a. Upper surface: Slightly darker than 74A. b. Under surface: Darker than 74C. 4. Flower size: Up to 6 cm or more in diameter.

G. *Reproductive organs.*—Flowers are monoecious. 1. Stamens: Five (5), broad and fused to form a tube around the ovary; tinged purple. 2. Anther: Hooded and cream colored. 3. Pollen: Cream colored. 4. Stigma: Five pointed star, colorless. 5. Styles: Very short. 6. Ovary: 5-celled, 4–5 mm long until fertilized. Grows to 1 cm or longer after fertilization; green.

Resistance to disease: Good resistance to common stem and root disease, Rizoctonia and Pythium. Botrysis may be a problem in humid or mist propagation environments, but no greater than with other New Guinea Impatiens cultivars.

I claim:

1. A new and distinct cultivar of Impatiens plant named Papete, as illustrated and described.

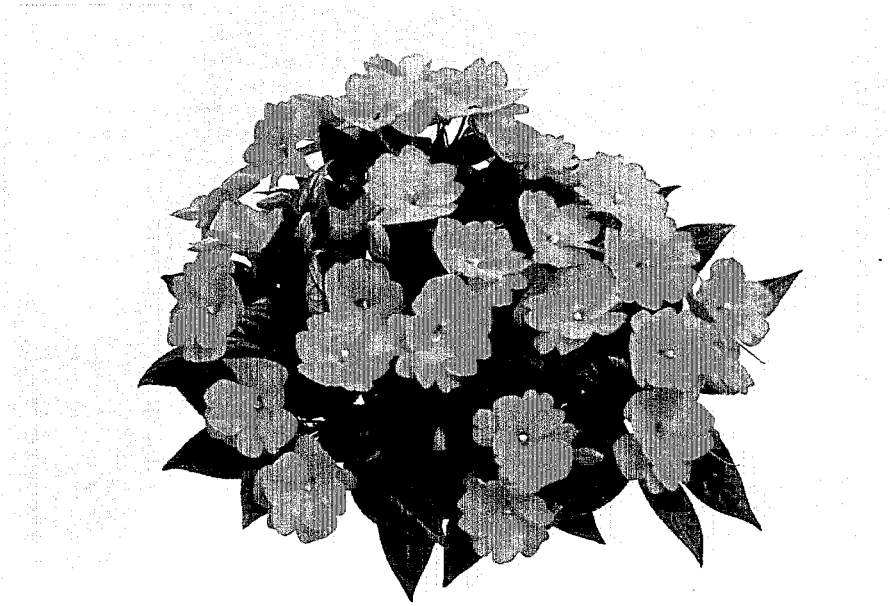

* * * * *